(12) United States Patent
Adams (10) Patent No.: US 6,387,114 B2
(45) Date of Patent: May 14, 2002

(54) GASTROINTESTINAL COMPRESSION CLIPS

(75) Inventor: Ronald Adams, Holliston, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/817,146

(22) Filed: Mar. 27, 2001

Related U.S. Application Data (62) Division of application No. 09/560,813, filed on Apr. 28, 2000, now Pat. No. 6,241,748.

(51) Int. Cl.$^7$ ................................................ A61B 17/08
(52) U.S. Cl. ................................................................ 606/220
(58) Field of Search ................................. 606/220, 213, 606/217, 157, 151, 139

(56) References Cited

U.S. PATENT DOCUMENTS

| | | |
|---|---|---|
| 4,485,816 A | 12/1984 | Krumme |
| 4,532,926 A | 8/1985 | O'Holla |
| 4,534,350 A | 8/1985 | Golden et al. |
| 4,665,906 A | 5/1987 | Jervis |
| 5,002,563 A | 3/1991 | Pyka et al. |
| 5,203,864 A | 4/1993 | Phillips |
| 5,269,809 A | 12/1993 | Hayhurst et al. |
| 5,395,391 A | 3/1995 | Essig et al. |
| 5,405,378 A | 4/1995 | Strecker |
| 5,423,858 A | 6/1995 | Bolanas et al. |
| 5,464,421 A | 11/1995 | Wortrich |
| 5,500,000 A * | 3/1996 | Feagin et al. ............ 606/232 |

FOREIGN PATENT DOCUMENTS

| | | |
|---|---|---|
| DE | 2 046 011 | 4/1971 |
| EP | 0 632 999 A1 | 1/1995 |
| GB | 1 560 282 | 2/1980 |
| WO | WO 96/16603 | 6/1996 |

* cited by examiner

Primary Examiner—Kevin T. Truong
(74) Attorney, Agent, or Firm—Kenyon & Kenyon (57) ABSTRACT

Medical devices and methods used to cause hemostasis of blood vessels located along the gastrointestinal tract. The medical devices include a clip having a stem, an anchor at a first end of the stem and a bolster at or near a second end of the stem. Methods of deploying the medical devices are disclosed.

17 Claims, 13 Drawing Sheets

GASTROINTESTINAL COMPRESSION CLIPS

The present Application is a Divisional of application Ser. No. 09/560,813, filed on Apr. 28, 2000 now U.S. Pat. No. 6,241,748, titled "Gastrointestinal Compression Clips".

FIELD OF THE INVENTION

The present invention relates to compression clips, and more specifically, to compression clips used to cause hemostasis of blood vessels located along the gastrointestinal tract.

BACKGROUND OF THE INVENTION

Gastrointestinal ("GI") bleeding is often associated with peptic ulcer disease and can be fatal if not treated immediately. For the estimated patient population of 10,000, approximately 2,000 will die during management of GI bleeding. This problem has prompted the development of a number of endoscopic therapeutic approaches to achieve hemostasis, such as the injection of sclerosing agents and contact thermo-coagulation techniques. Although such approaches are often effective, bleeding continues for many patients and emergency corrective surgery therefore becomes necessary. Because surgery is an invasive technique that is associated with many undesirable side effects, there exists the need for highly effective, less invasive procedures.

Mechanical hemostatic devices are used in various parts of the body, including GI applications. Such devices are typically in the form of clamps, clips, staples, sutures, etc., which are able to apply sufficient constrictive forces to blood vessels so as to limit or interrupt blood flow. One of the problems associated with conventional hemostatic devices, however, is that they are delivered using rigid-shafted instruments via incision or trocar cannula. Moreover, conventional endoscopic hemostatic devices are not generally strong enough to consistently control GI bleeding.

SUMMARY OF THE INVENTION

The present invention provides medical devices and methods of deploying such medical devices for causing the hemostasis of blood vessels located along the gastrointestinal tract. Each of the medical devices of the present invention comprises a clip that includes a stem having a first end and a second end; an anchor at the first end of the stem; and a bolster at or near the second end of the stem. In one embodiment of the invention, the stem has at least one transverse hole therein, and the bolster is slidable about the stem and includes a flap adapted to be inserted into the transverse hole. In a second embodiment of the invention, the stem has at least one engaging member extending therefrom, and the bolster has a central opening that is wider than the stem at a location where the engaging member is absent but is more narrow than the stem at a location where the engaging member is present. In a third embodiment of the invention, the stem has at least one dimple therein and the bolster has at least one locking element attached thereto by a spring, wherein the locking element fits within the dimple. In a fourth embodiment of the invention, the bolster is fixed at the second end of the stem.

One advantage of the present invention is that it provides a medical device that, when deployed, creates sufficient tissue compression to hemostatically control GI bleeding.

Another advantage of the present invention is that it provides a consistent, reproducible means for controlling GI bleeding.

Another advantage of the present invention is that it provides a definitive solution to the problem of GI bleeding.

Yet another advantage of the present invention is that it provides a means to control GI bleeding without resorting to open or laparoscopic surgical techniques.

DETAILED DESCRIPTION

The present invention provides medical devices and methods of deploying such medical devices for causing the hemostasis of blood vessels located along the gastrointestinal tract. The medical devices each comprise a clip comprising a stem having a first end and a second end, an anchor at the first end of the stem, and a bolster. The bolster is herein disclosed to be "at or near" the second end of the stem in that the bolster is either fixed at the second end of the stem, or positioned at a location between the second and first ends of the stem.

Figure 1:
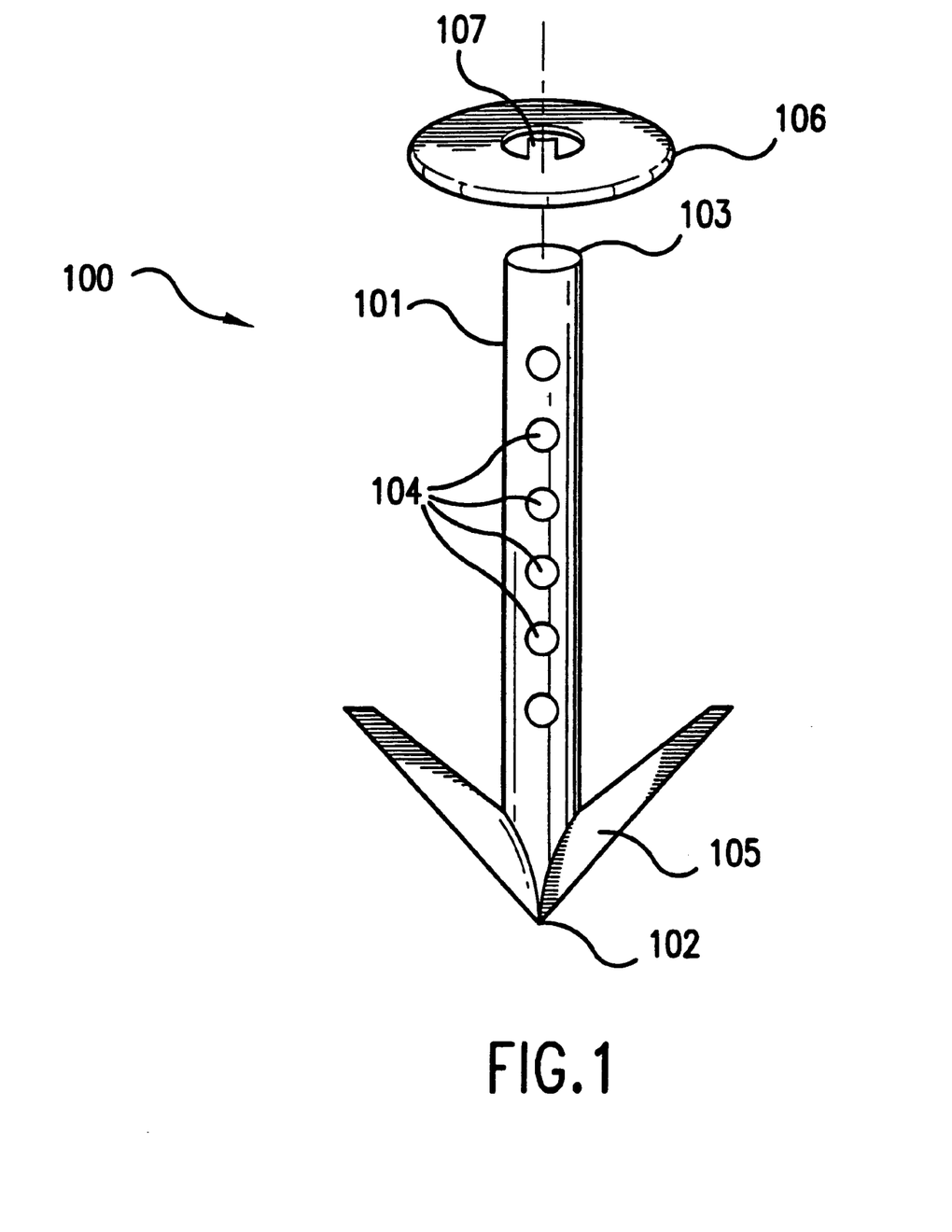
FIG. 1 illustrates a first embodiment of the medical device of the present invention.

In a first embodiment of the invention as shown in FIG. 1, medical device 100 includes a stem 101 having first end 102 and second end 103. Stem 101 has at least one transverse hole 104 therein of any suitable shape (e.g. circular, rectangular, square, etc.). Stem 101 is further characterized by an anchor 105 at its first end 102. Anchor 105 comprises at least one anchor member that extends away from stem 101 and towards second end 103. Medical device 100 also comprises a bolster 106, which includes a flap 107 adapted to be inserted into hole 104.

The medical devices of the present invention are made from any suitable biocompatible polymeric or metallic material. It is preferred, however, that stem 101 be made from an elastic material such as stainless steel, nitinol, or any suitable polymeric material such as polyethylene. The elasticity of stem 101 permits anchor 105 to be compressed to facilitate delivery within a body lumen. It is also preferred, although not necessary, that bolster 106 be made from the same material as stem 101. Bolster 106 is made from a material, however, that is rigid enough so that, when in use, flap 107 remains in a selected hole 104 to apply pressure against a GI wall. Flap 107 is optionally attached to bolster 106 by a "one-way" hinge or a similar mechanism that allows bolster to be moved towards first end 102 but prevents movement towards second end 103 once flap 107 is inserted into a desired hole 104.

Figure 2:
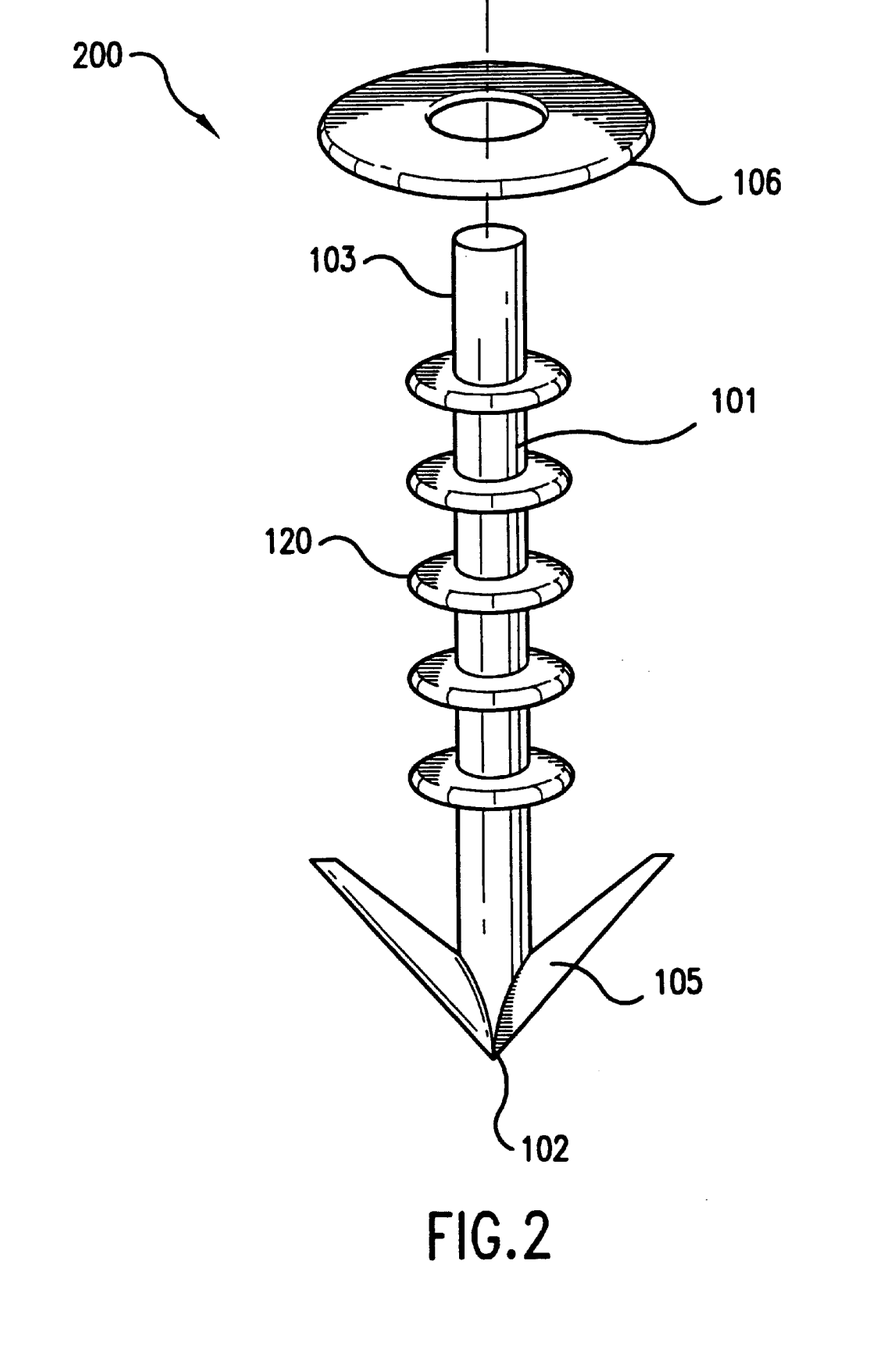
FIG. 2 illustrates a second embodiment of the medical device of the present invention.

In a second embodiment of the invention, stem 101 of medical device 200 has at least one engaging member 120 extending therefrom as shown in FIG. 2. Where multiple engaging members 120 are used, they are arranged in any suitable configuration, such as the series of engaging member pairs shown in FIG. 2. In this embodiment, bolster 106 has a central opening that is wider than the stem at a location where engaging member 120 is absent but is more narrow than the stem at a location where engaging member 120 is present.

The materials used for stem 101 and bolster 106 of medical device 200 are selected to facilitate the movement of bolster 106 over engaging members 120 until bolster 106 is positioned at a desired location along stem 101. For example, bolster 106 is elastically deformable enough to be pushed over engaging members 120 without plastically deforming, or alternatively, engaging members 120 are elastically deformable enough so as to allow the passage of bolster 106 towards first end 102 of stem 101 without causing the plastic deformation of engaging members 120.

Figure 3A:
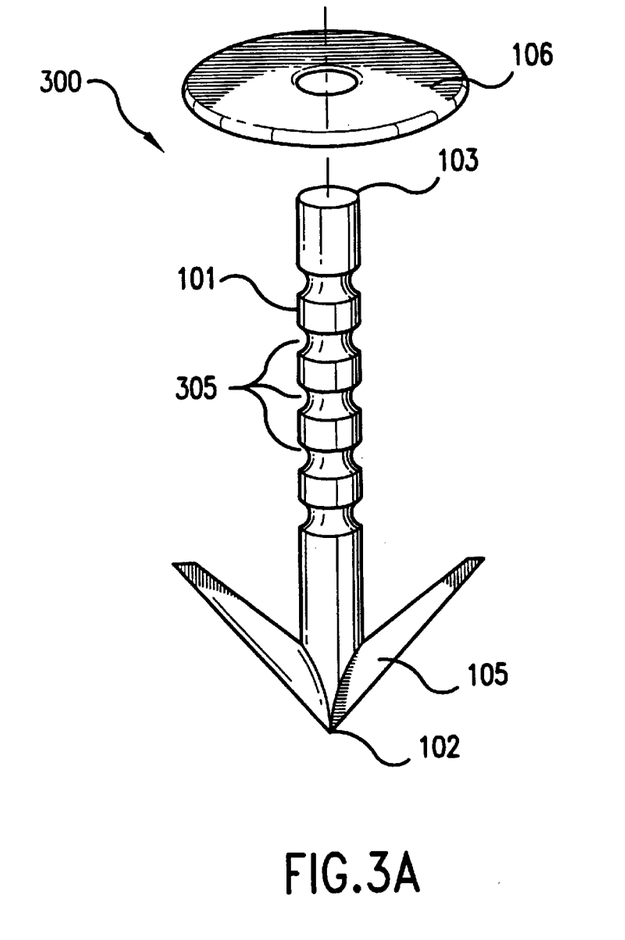
FIGS. 3A–3B illustrate a third embodiment of the medical device of the present invention.
Figure 3B:
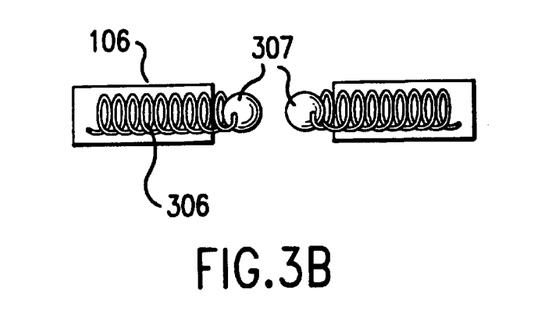

In a third embodiment of the invention, stem 101 of medical device 300 includes at least one dimple 305, as shown in FIG. 3A. Where multiple dimples are used, they are arranged in any suitable configuration such as the series of dimple pairs shown in FIG. 3A. Alternatively, dimples 305 are annular cavities around the circumference of stem 101. Bolster 106 includes locking elements 307, such as spheres, that are attached to bolster 106 by springs 306, as shown in FIG. 3B. Springs 306 are of any suitable configuration, although they are shown as coils in FIG. 3B. Locking elements 307 fit within dimples 305 for placing bolster 106 at a desired location along stem 101. Springs 306 are of sufficient strength to keep locking elements 307 within dimples 305 when medical device 300 is in use. Springs 306 and locking elements 307 are made from any suitable material, such as, for example, steel or nitinol.

Figure 4:
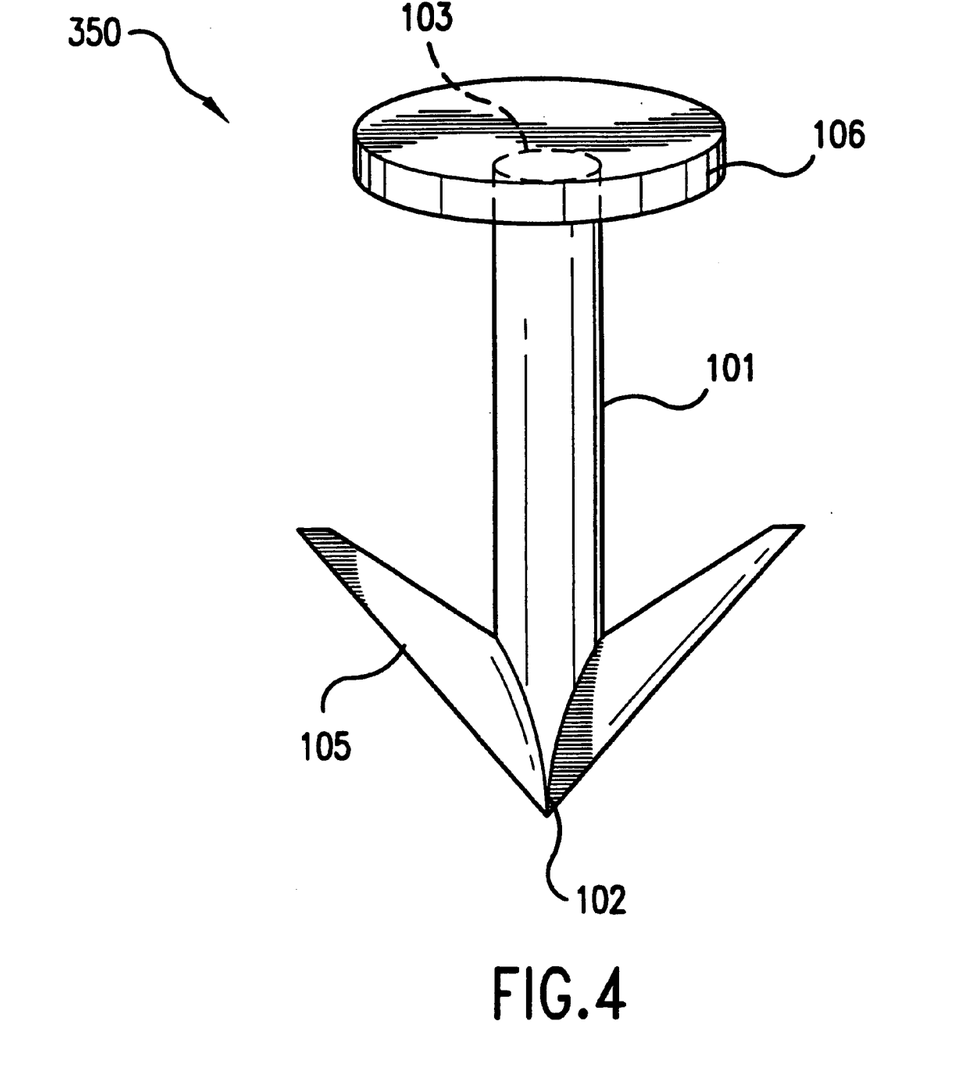
FIG. 4 illustrates a fourth embodiment of the medical device of the present invention.

In a fourth embodiment of the invention, medical device 350 comprises a bolster 106 that is fixed to stem 101, as shown in FIG. 4. Bolster 106 is an integral part of device 350 or is rigidly attached to stem 101, for example. Like the embodiment shown in FIGS. 1 and 2, it is preferred that stem 101 of device 350 be made from an elastic material to facilitate delivery within a body lumen.

Figure 5A:
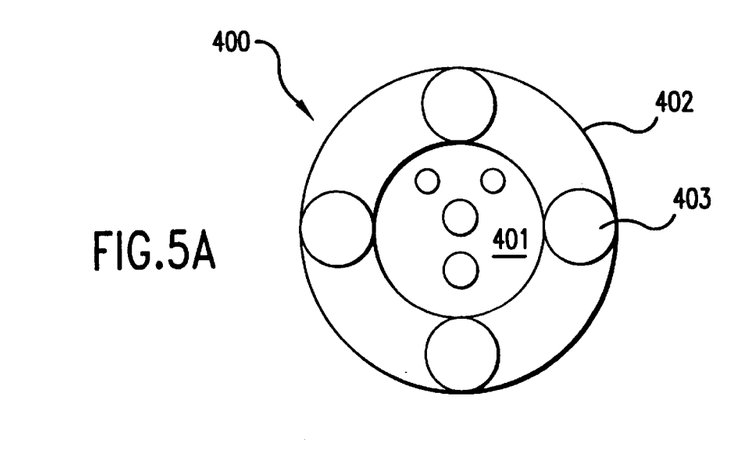
FIG. 5A shows an end view of an example of a delivery device, in accordance with the present invention.
Figure 5B:
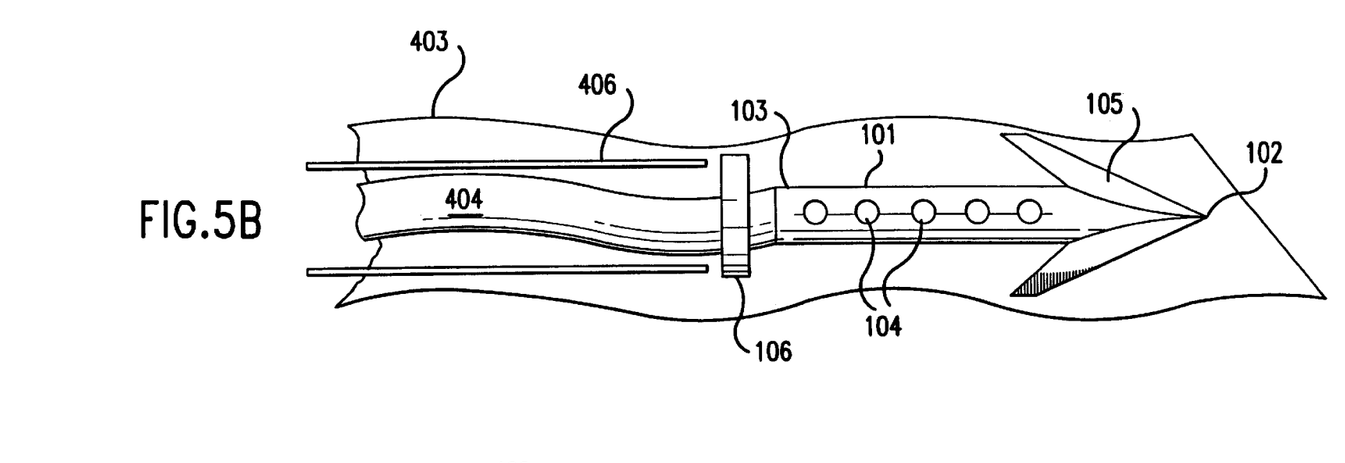
FIGS. 5B–5E illustrate a method of deploying a medical device having a moveable bolster, in accordance with the present invention.

The deployment of medical device 100 to a location along the GI tract is accomplished by any suitable means. For example, deployment of device 100 is accomplished with the use of delivery device 400 as shown in FIGS. 5A–5E. Delivery device 400 comprises an endoscope 401 having an outer sheath 402 for containing at least one delivery tube 403. Endoscope 401 is preferably orally inserted into the GI tract, although it is also able to be inserted rectally. "Endoscope" as used herein is intended to include similar instrumentation such as a gastroscope or duodenoscope. Endoscope 401 is typically about 10 mm in diameter, and the maximum diameter for outer sheath 402 is typically about 20 mm. Delivery tube 403 houses medical device 100 such that anchor 105 is contained by sleeve 403 in a compressed or "folded" configuration, as shown in FIG. 5B.

Figure 5C:
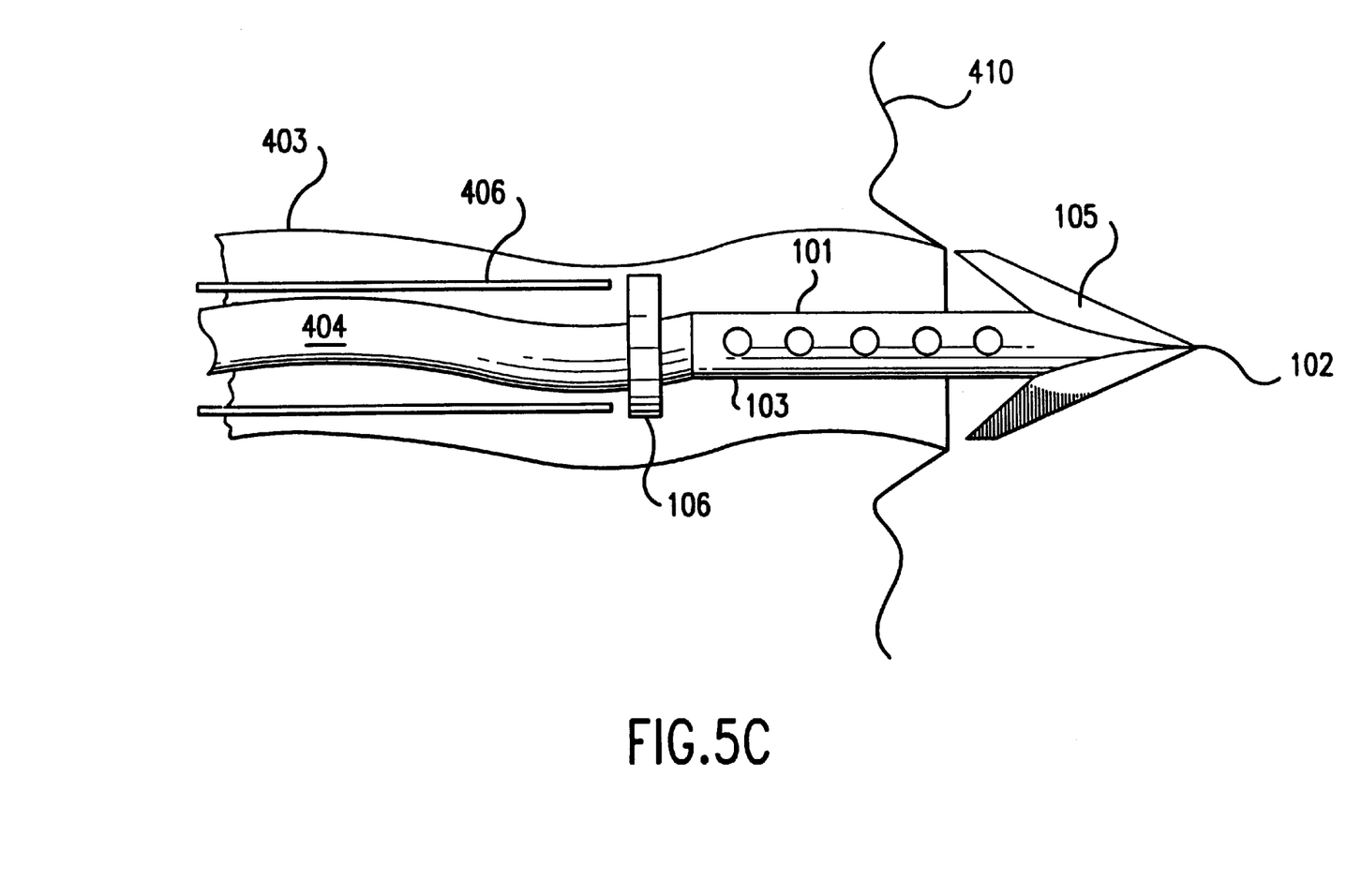
Figure 5D:
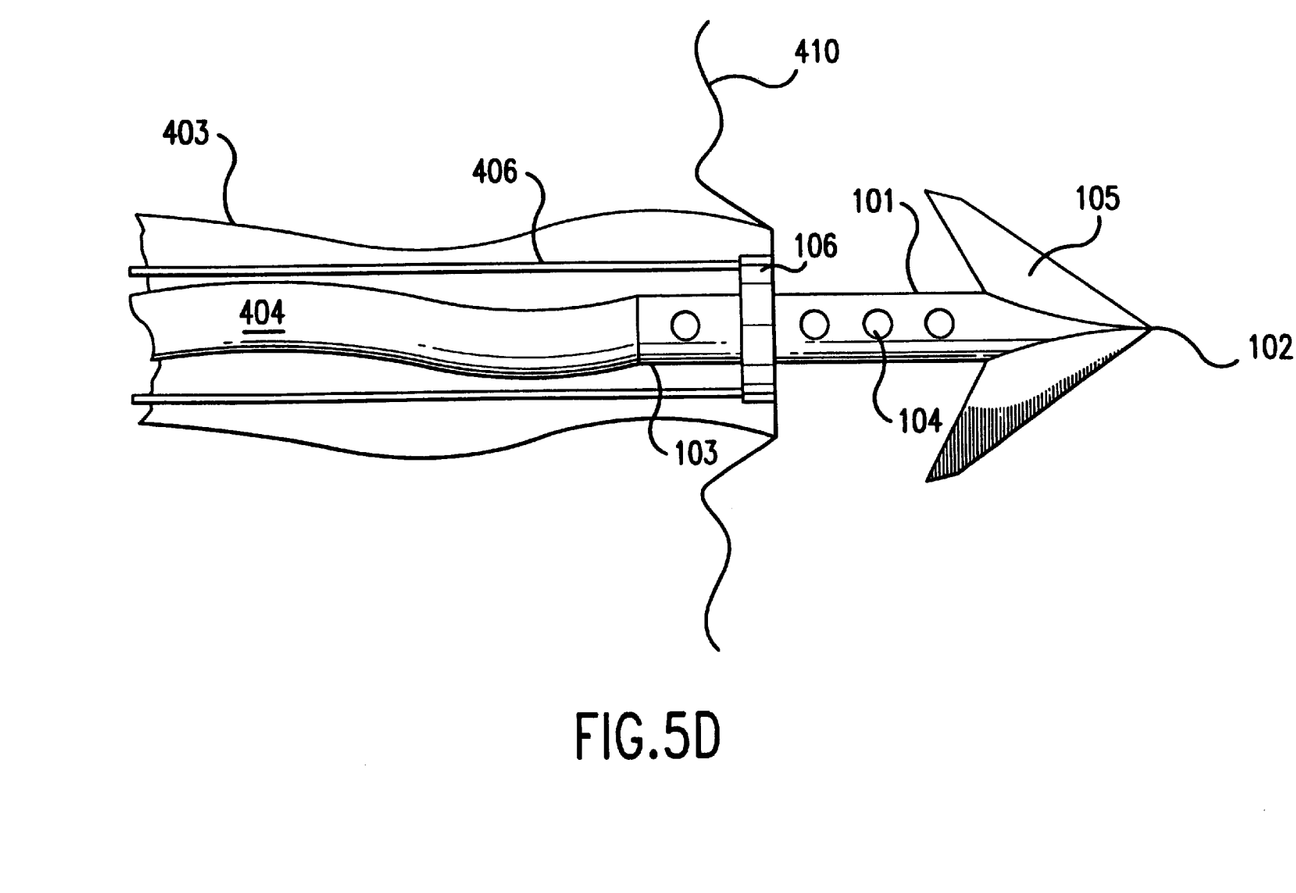

When a target location along the GI tract is identified by endoscope 401, the end of delivery device 400 is positioned against or adjacent to the GI wall 410. Stem 101 is pushed out of sleeve 403 by stem pusher 404 such that the first end 102 of stem 101 pierces the GI wall 410, as shown in FIG. 5C. Once stem 101 is extended to a desired depth within GI wall 410, bolster pusher 406 is used to push bolster 106 over stem 101 and towards first end 102. As bolster 106 proceeds towards first end 102, an increasing pressure is applied to the tissue between GI wall 410 and anchor 105. Anchor 105 is thus urged back towards GI wall 410, resulting in the expansion of anchor 105 to its "unfolded" configuration and thus locking stem 101 in its position as shown in FIG. 5D. When sufficient pressure is applied to the GI wall 410 to cause hemostasis of an adjacent bleeding blood vessel, flap 107 of bolster 106 is locked into the at least one transverse hole 104 in stem 101. As such, bolster 106 maintains pressure of the GI tissue and permanently induces hemostasis of the adjacent blood vessels. Medical device 100 is shown in its deployed configuration in FIG. 5E.

Medical devices 200 and 300 are deployed, for example, via the method described and shown for medical device 100. Although bolster 106 is slidable over stem 101 for each of devices 200 and 300, the force exerted by the GI wall 410 on bolster 106 after deployment is not great enough to move bolster 106 back towards second end 103 of stem 101.

Figure 5E:
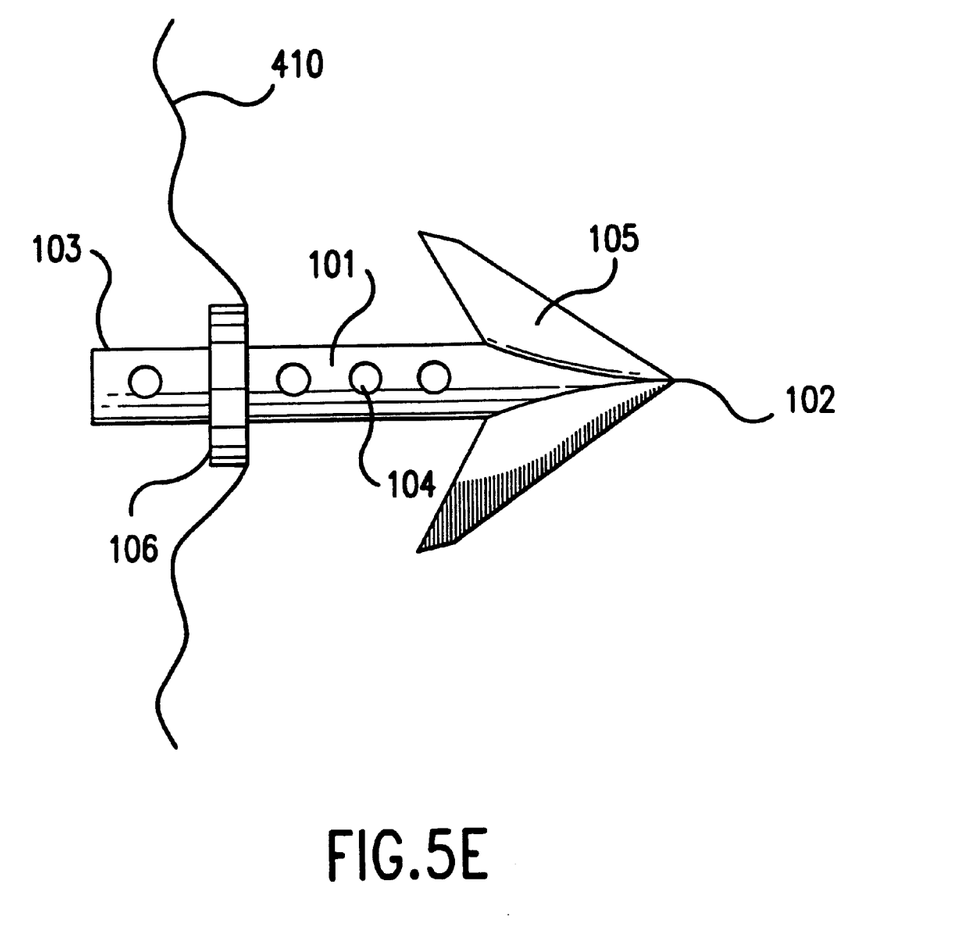
Figure 6A:
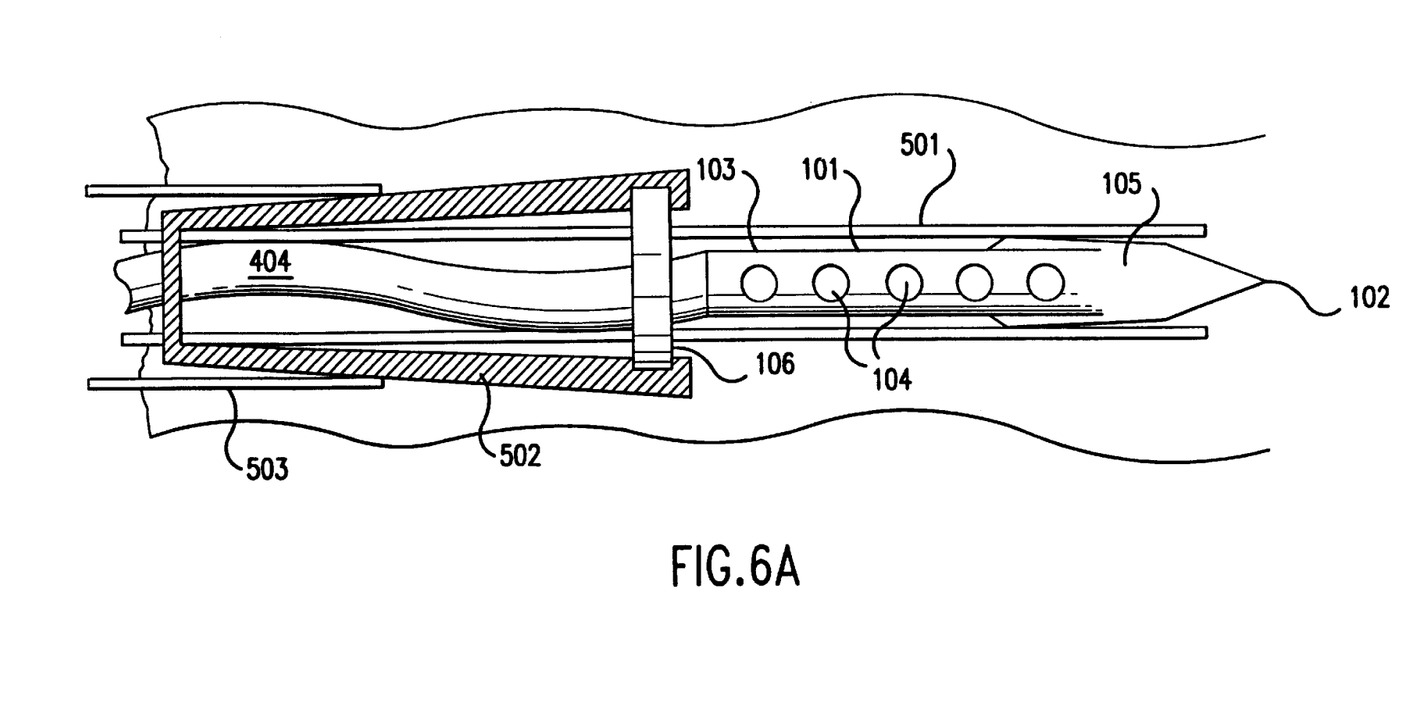
FIGS. 6A–6C illustrate an alternative method of deploying a medical device in accordance with the present invention.
Figure 6B:
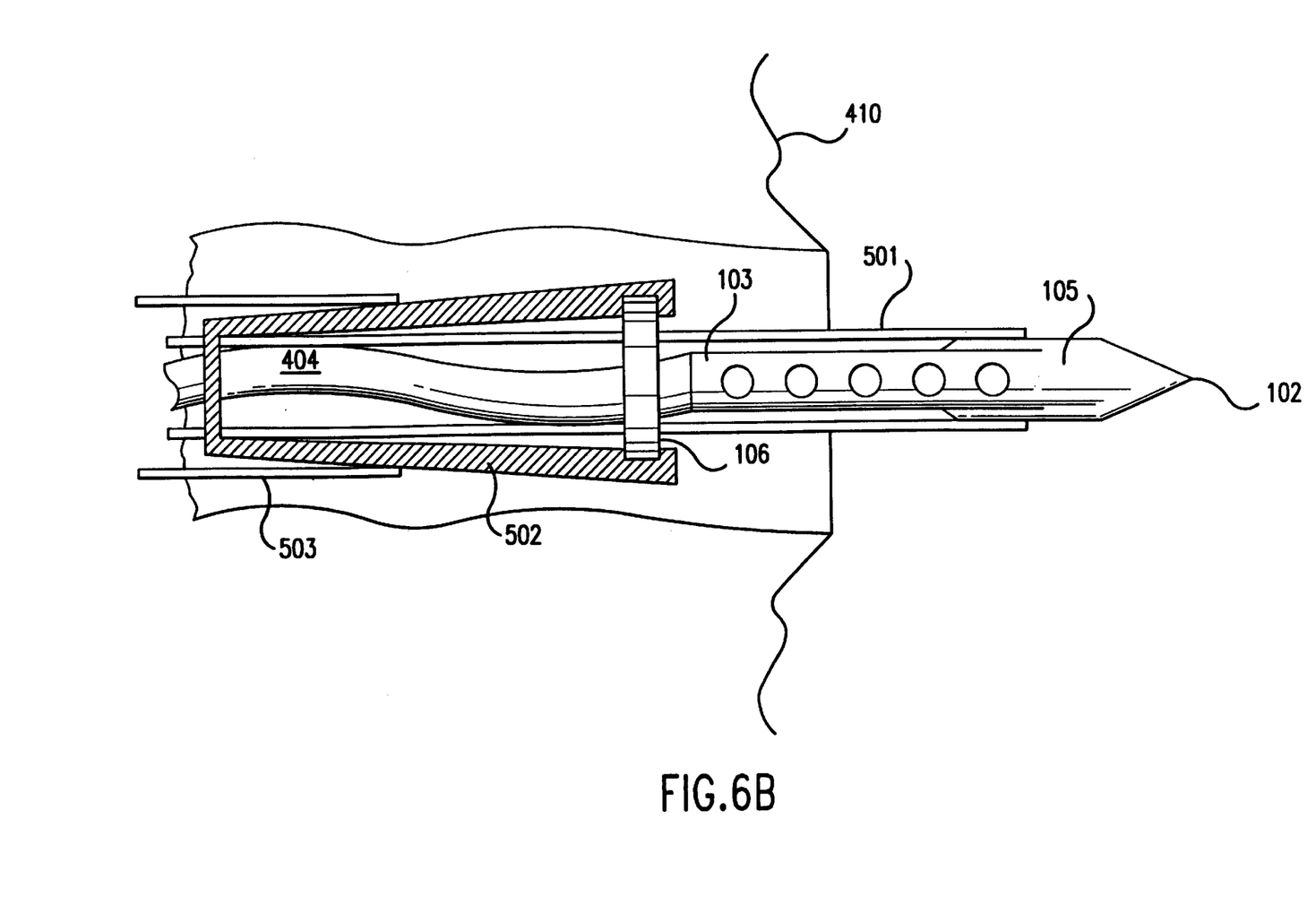
Figure 6C:
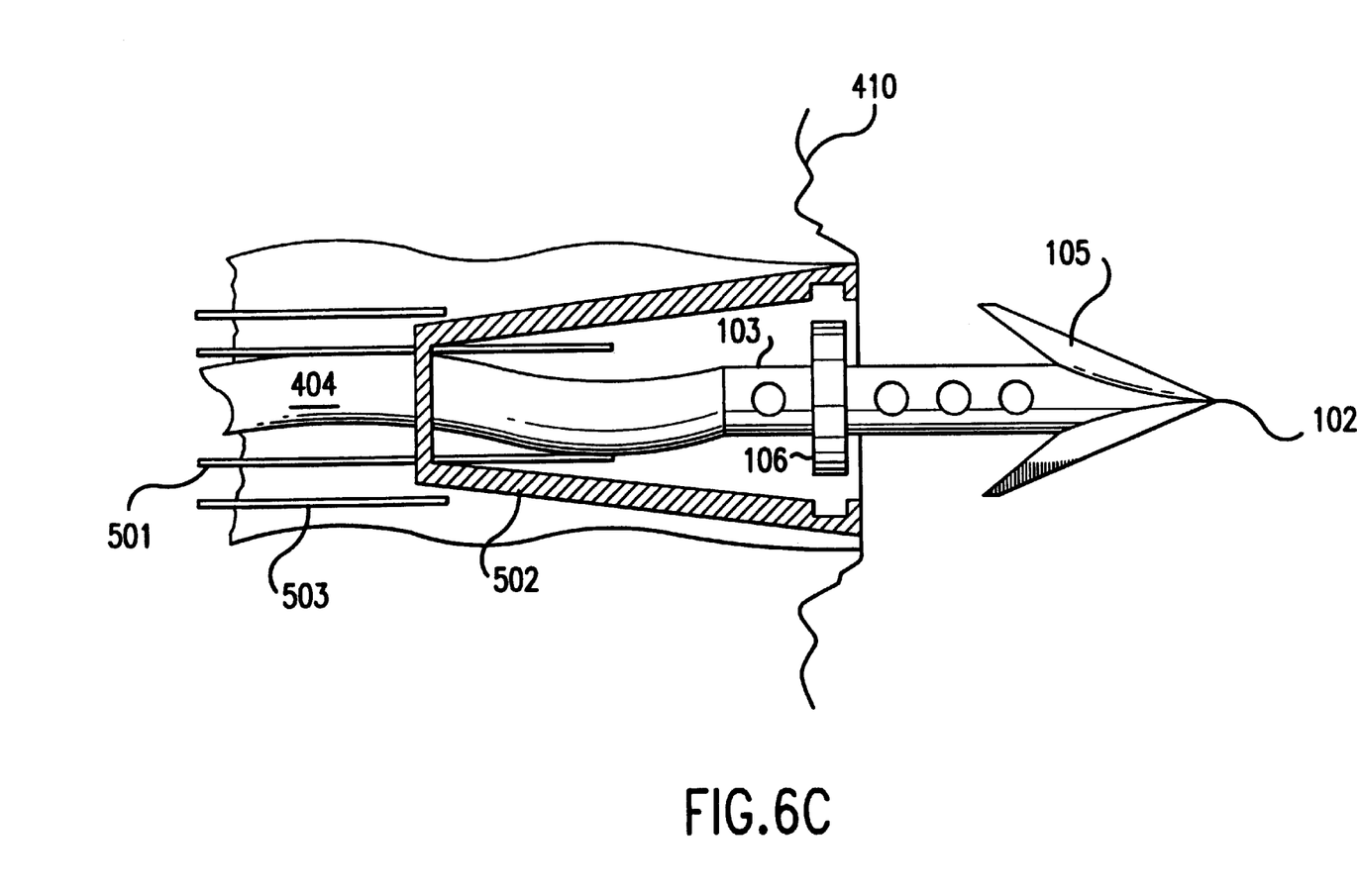

As an alternative example, medical devices 100, 200 and 300 are deployed as shown in FIGS. 6A–6C. For example, the anchor of medical device 100 is held in a compressed configuration by compression sheath 501. Bolster 106 is disposed about compression sheath 501 and its position is controlled by the movement of clip 502 when bolster 106 is engaged by clip 502. The first end 102 of stem 101 is used to pierce GI wall 410 while the anchor members of anchor 105 are held in a compressed configuration, as shown in FIG. 6B. After stem 101 has been inserted to a desired depth within GI wall 410, compression sheath 501 is retracted to allow the anchor members of anchor 105 to expand to an unfolded configuration, as shown in FIG. 6C. Clip 502 is advanced by a pusher bar or the like such that bolster 106 is moved over stem 101 until a desired pressure is applied to GI wall 410. Locking collar 503 is then retracted, allowing clip 502 to disengage bolster 106, as shown in FIG. 6C. Medical device 100 thus deployed is shown in FIG. 5E.

Figure 7A:
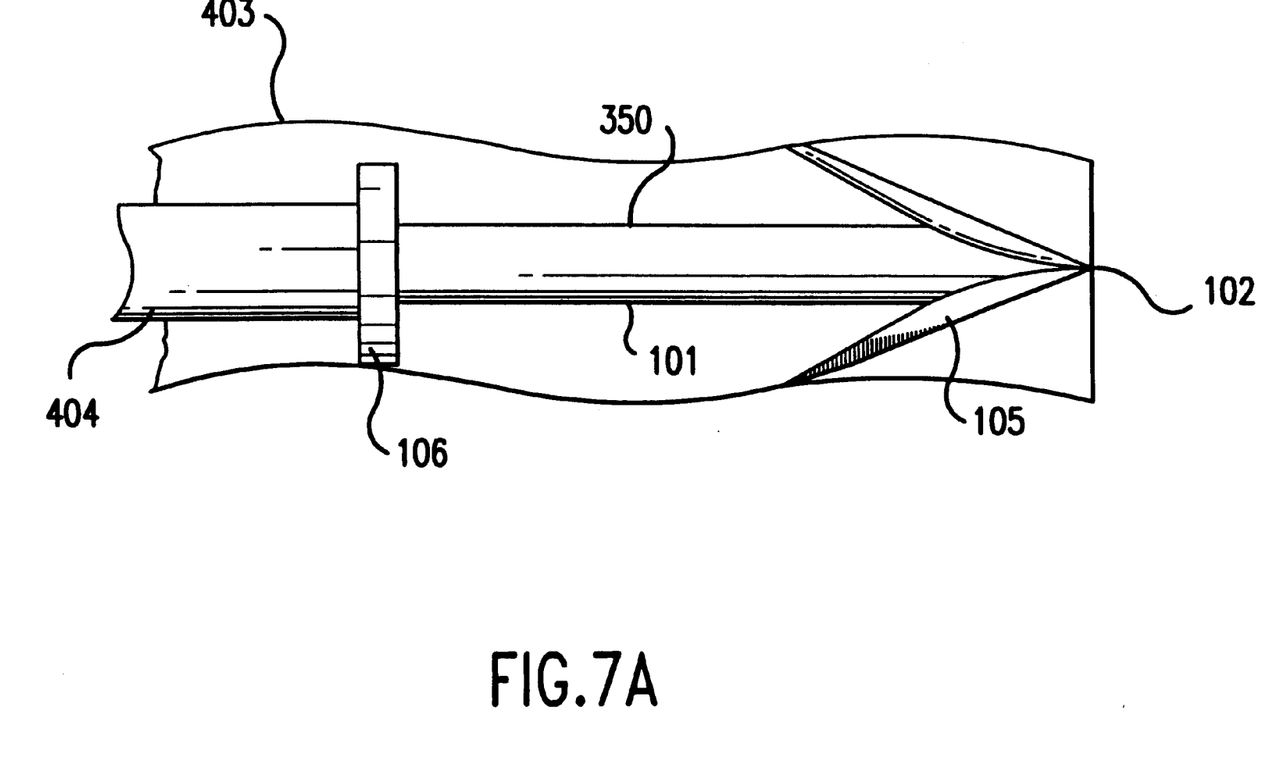
FIGS. 7A–7C illustrate a method of deploying a medical device having a fixed bolster, in accordance with the present invention.
Figure 7B:
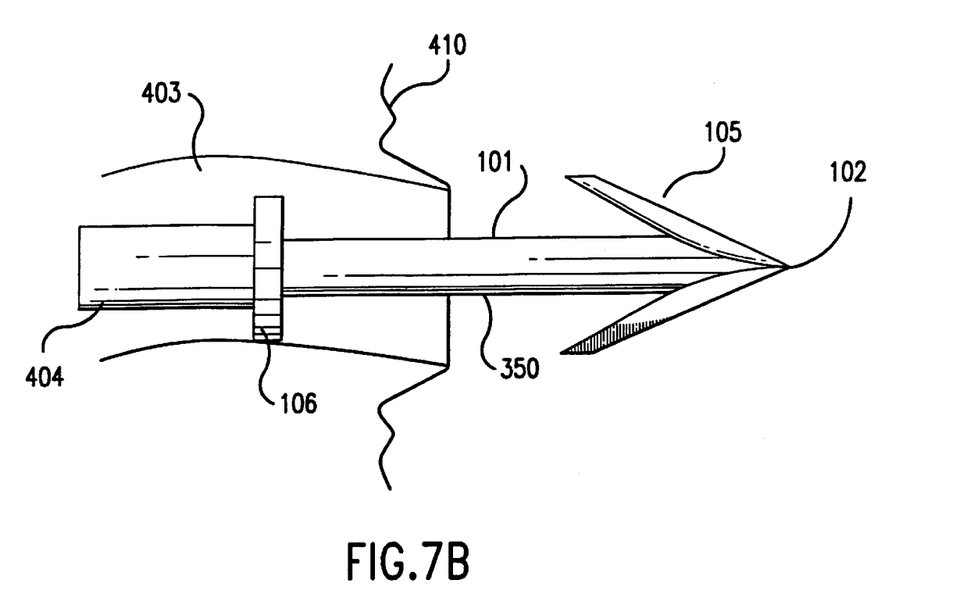
Figure 7C:
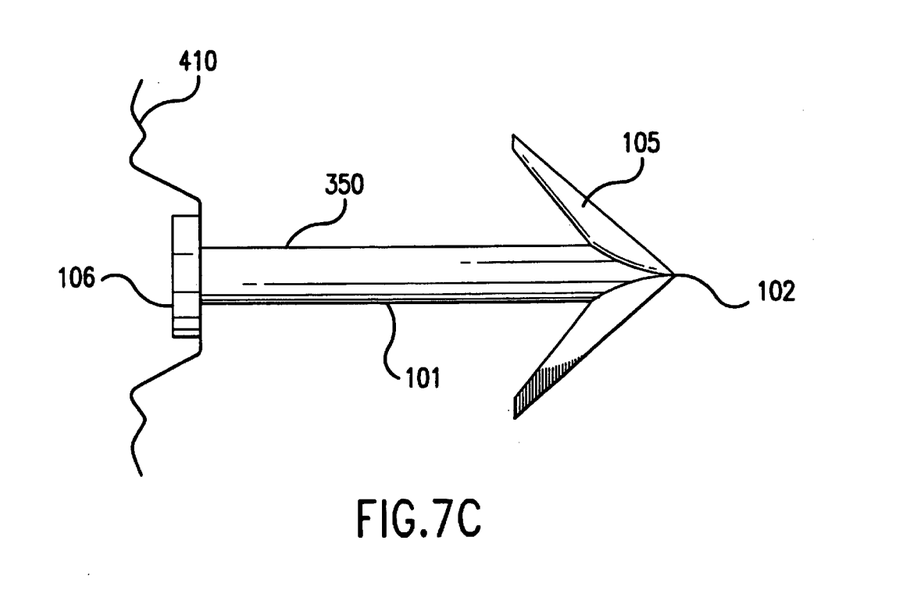

Medical device 350, having a bolster that is fixed to its stem, is deployed with the use of delivery device 400, for example. In the case of device 350, however, multiple pusher bars are not necessary and the device is loaded into delivery tube 403 as shown in FIG. 7A. Device 350 is pushed out of sleeve 403 by device pusher bar 404 such that the first end 102 of stem 101 pierces the GI wall 410, as shown in FIG. 7B. Once stem 101 is extended to a desired depth within GI wall 410, which is typically the entire length of stem 101, device 350 is released from pusher bar 404. Because of the pressure in the tissue between GI wall 410 and first end 102 of stem 101, anchor 105 is urged back towards GI wall 410, thus resulting in the expansion of anchor 105 to its "unfolded" configuration. Device 350 is thus locked in its position as shown in FIG. 7C.

The medical devices of the present invention are of any suitable size, although it is preferred that stem 101 be about 0.5–2 cm, preferably about 1 cm in length, and about 0.5–5 mm, preferably about 2 mm in diameter.

The medical devices of the present invention are preferably located within about 1 cm from any bleeding blood vessel. When used to stop bleeding from an ulcer bed, the medical devices of the present invention are located within about 5 mm, preferably about 2 mm, and more preferably about 1 mm from the edge of an ulcer bed. As many as six or more of the medical devices of the present invention are used to surround an ulcer bed to stop the bleeding thereof.

The present invention provides a reliable, definitive treatment for the problem of gastrointestinal bleeding. When deployed in accordance with the present invention, the clips provide sufficient strength to produce permanent hemostasis.

It will be obvious to those skilled in the art, having regard to this disclosure, that other variations on this invention beyond those specifically exemplified here may be made. Such variations are, however, to be considered as coming within the scope of this invention as limited solely by the following claims.

What is claimed is:

1. A medical device for causing the hemostasis of a blood vessel located along the gastrointestinal tract, said medical device comprising:
    a stem having a first end and a second end, wherein said stem has at least one transverse hole therein;
    an anchor at the first end of said stem; and
    a movably positionable bolster at or near the second end of said stem, wherein said bolster includes:
    a central opening, wherein said central opening is wider than said stem; and
    a flap adapted to be inserted into said at least one transverse hole in said stem.

2. The medical device of claim 1, wherein said medical device comprises stainless steel.

3. The medical device of claim 1, wherein said medical device comprises nitinol.

4. The medical device of claim 1, wherein said medical device comprises a polymeric material.

5. The medical device of claim 1, wherein said stem is approximately 0.5–2 centimeters in length.

6. The medical device of claim 1, wherein said stem is approximately 0.5–5 millimeters in diameter.

7. A medical device for causing the hemostasis of a blood vessel located along the gastrointestinal tract, said medical device comprising:
    a stem having a first end and a second end;
    an anchor at the first end of said stem, wherein said anchor comprises at least one anchor member extending away from said stem and towards the second end of said stem, and further wherein a distance between a first end proximal to said stem of said at least one anchor member and a second end distal from said stem of said at least one anchor member is at least twice the diameter of said stem; and
    a bolster at or near the second end of said stem, wherein said bolster is rigidly attached to said stem.

8. The medical device of claim 7, wherein said medical device comprises stainless steel.

9. The medical device of claim 7, wherein said medical device comprises nitinol.

10. The medical device of claim 7, wherein said medical device comprises a polymeric material.

11. The medical device of claim 7, wherein said stem is approximately 0.5–2 centimeters in length.

12. The medical device of claim 7, wherein said stem is approximately 0.5–5 millimeters in diameter.

13. A system to achieve the hemostasis of a blood vessel located along the gastrointestinal tract, said system comprising:
    a clip, said clip comprising:
        a stem having a first end and a second end;
        an anchor at the first end of said stem, wherein said anchor comprises at least one anchor member extending away from said stem of said clip and towards the second end of said stem, and further wherein a distance between a first end proximal to said stem of said at least one anchor member and a second end distal from said stem of said at least one anchor member is at least twice the diameter of said stem; and
        a bolster at or near the second end of said stem, wherein said bolster is rigidly attached to said stem; and
    a delivery device.

14. The system of claim 13, wherein said delivery device comprises:
    an endoscope; and
    a delivery tube adjacent to said endoscope wherein said clip is removably positionable within said delivery tube.

15. The system of claim 14, further comprising an outer sheath surrounding said endoscope.

16. The system of claim 15, wherein said delivery tube is positioned between said endoscope and said outer sheath.

17. The system of claim 14, further comprising a pusher bar, said pusher bar movably disposed within said delivery tube and releasably engageable with said bolster.

* * * * *